United States Patent [19]

Costello et al.

[11] Patent Number: 5,977,422
[45] Date of Patent: *Nov. 2, 1999

[54] ORGANOALUMINUM CATALYSIS OF ALKYLATION REACTIONS

[75] Inventors: Steven A. Costello, Lake Jackson; Douglas L. Potts, Angleton; Randall F. Pogue, Friendswood, all of Tex.

[73] Assignee: The Dow Chemical Company, Midland, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/871,742

[22] Filed: Jun. 9, 1997

[51] Int. Cl.$^6$ .............................. C07C 1/20; C07C 15/00; C07C 2/64; C07C 2/70
[52] U.S. Cl. ......................... 585/409; 585/25; 585/407; 585/408; 585/410; 585/446; 585/459; 585/462; 585/461
[58] Field of Search ............................ 585/25, 407, 408, 585/409, 410, 446, 459, 462, 461

[56] References Cited

U.S. PATENT DOCUMENTS

| | | | |
|---|---|---|---|
| 3,522,324 | 7/1970 | Butte, Jr. et al. | 260/671 |
| 3,787,512 | 1/1974 | Nelson | 260/668 |
| 3,875,249 | 4/1975 | Nelson | 260/651 HA |
| 4,002,645 | 1/1977 | Sonnenberg | 260/345.2 |
| 4,016,280 | 4/1977 | Menge et al. | 424/267 |
| 4,022,786 | 5/1977 | Hackmack et al. | 260/293.72 |
| 4,062,805 | 12/1977 | Franck et al. | 252/430 |
| 4,092,371 | 5/1978 | Franck et al. | 260/671 |
| 4,101,510 | 7/1978 | Spanswick | 260/45.75 |
| 4,155,944 | 5/1979 | Seidov et al. | 585/457 |
| 4,251,675 | 2/1981 | Engel | 585/422 |
| 4,424,169 | 1/1984 | Swedo | 260/505 |
| 4,593,086 | 6/1986 | Jansons et al. | 528/173 |
| 4,611,033 | 9/1986 | Maresca | 525/419 |
| 4,613,687 | 9/1986 | Knofel et al. | 560/359 |
| 4,665,246 | 5/1987 | Anderson | 585/320 |
| 4,710,562 | 12/1987 | Maresca | 525/125 |
| 4,716,211 | 12/1987 | Clendinning et al. | 528/126 |
| 4,731,484 | 3/1988 | Walters | 568/331 |
| 5,077,356 | 12/1991 | Masaharu et al. | 525/534 |
| 5,132,477 | 7/1992 | Ho et al. | 585/467 |
| 5,136,114 | 8/1992 | Arlt | 570/192 |
| 5,186,864 | 2/1993 | Commandeur et al. | 252/581 |
| 5,227,556 | 7/1993 | Benton et al. | 585/323 |
| 5,250,657 | 10/1993 | Tsuchida et al. | 528/383 |

*Primary Examiner*—Walter D. Griffin
*Assistant Examiner*—In Suk Bullock
*Attorney, Agent, or Firm*—Dale H. Schultz

[57] ABSTRACT

This invention relates to an improved catalytic process for the alkylation of benzene or substituted benzene with alkyl halides for the continuous production of diarylalkanes or substituted derivatives thereof using ethylaluminum dichloride or methylaluminum dichloride as an organoaluminum dichloride catalyst. A process and apparatus are provided for reacting either benzene (or a substituted benzene compound) together with either an alkyl halide or an aromatic halide.

8 Claims, 5 Drawing Sheets

ORGANOALUMINUM CATALYSIS OF ALKYLATION REACTIONS

FIELD OF THE INVENTION

This invention relates to an improved catalytic process for the alkylation of benzene or substituted benzene with alkyl halides for the continuous production of diarylalkanes or substituted derivatives thereof using methylaluminum dichloride or ethylaluminum dichloride as the organoaluminum catalyst. In one set of useful embodiments, diphenylmethane is synthesized through the reaction of benzene and dichloromethane.

BACKGROUND

Diphenylmethane, also known as 1,1'-methylene-bis-benzene, is useful for the production of heat transfer fluids, aromatic solvents, fragrances, and monomers for polycarbonate resins.

Various processing schemes comprising alkylation and/or transalkylation reactions are known to produce monoalkylaromatic or polyalkylaromatic products (such as diphenylmethane) in high yield. However, one of the issues burdening existing processes is the production of undesirable by-products through secondary reactions. Examples of such by-products produced in conjunction with monoalkylaromatic or polyalkylaromatic products include alkylating agent oligomers, heavy polyaromatic compounds, and polyalkylated compounds.

Another issue burdening existing processes concerns the use of Friedel-Crafts catalysts based on aluminum chloride and other Lewis, Brönsted, or Brönsted-Lewis types of acids; commercial technology associated with Friedel-Crafts catalysis based on aluminum chloride is subject to more than one disadvantage. In such systems, selectivity to desired products in Friedel-Crafts reactions is frequently limited, and complex multicomponent mixtures frequently result from affiliated competitive reactions. Friedel-Crafts catalysts are corrosive, requiring use of expensive metals in plant construction. These catalysts also generally require the use of a water or acid gas co-catalyst which produces a corrosive sludge by-product. These and other problems associated with Friedel-Crafts catalysts can be avoided by the use of organoaluminum Lewis acids with certain alkylating agents.

It is known that aromatic hydrocarbons can be alkylated in the presence of alkylaluminum halide reagents. Such technology is discussed in U.S. Pat. No. 3,787,512 to G. E. Nelson entitled "Preparation of Aromatic Hydrocarbons" which refers to the alkylation of benzene or alkylated benzene by an alkyl halide in the presence of an alkylaluminum halide. This patent is incorporated herein by reference in discussion of the background of this invention. U.S. Pat. No. 3,875,249 to G. E. Nelson describes a "process for alkylating an aromatic hydrocarbon by reacting a haloalkane with either benzene or an alkyl benzene . . . in the presence of an alkylaluminum halide catalyst". More specifically, U.S. Pat. No. 3,787,512 indicates combination of methylene chloride and benzene in the presence of methylaluminum sesquichloride and also methylene iodide and benzene in the presence of ethylaluminum sesquichloride to make diphenylmethane.

The Applicants for the present invention, however, have discovered that the synthesis of diphenylmethane from benzene and methylene chloride in the presence of methylaluminum dichloride or ethylaluminum dichloride affords some clear and distinguishing benefits; these benefits indicate that organoaluminum dichlorides in general have distinct and special usefulness in alkylations which are reactively similar to the focal diphenylmethane synthesis. In this regard, methylaluminum and ethylaluminum dichloride catalysts greatly increase the rate of reaction of benzene and methylene chloride compared to the catalyst technologies utilizing aluminum chloride or the organoaluminum sesquichlorides specifically cited by Nelson in U.S. Pat. No. 3,787,512. In practice, the reaction of methylene chloride and benzene in the presence of either methylaluminum sesquichloride or ethylaluminum sesquichloride in an appropriate reaction environment shows an "induction time" (where essentially no or very little conversion to diphenylmethane is apparent) lasting from 30–60 minutes after initial contact of the reactants. In contrast, and in an unexpected result, Applicants in the present invention discovered that the reaction of benzene and methylene chloride in the presence of either methylaluminum dichloride or ethylaluminum dichloride occurred immediately and rapidly such that the conversion to diphenylmethane was complete in a commercially attractive period of time (for methylaluminum dichloride, ~75% complete in 15 minutes).

In accordance with the present invention, there has been discovered a process for decreasing the selectivity for undesirable by-products while using an organoaluminum catalyst which affords a high yield of the alkylate of interest over a sustainable and commercially attractive period of time. One particular advantage of the process of the present invention derives from the utilization of alkylation at high temperatures (greater than 100 degrees Celsius for this type of reaction), because a commercially attractive period of time for completion of the reaction is provided even as high selectivity for useful products such as diphenylmethane is achieved.

SUMMARY OF THE INVENTION

The present invention provides a system and method for the preparation of a diarylalkane by reacting together benzene and either an alkyl halide or an aromatic halide in the presence of ethylaluminum dichloride or methylaluminum dichloride. In one preferred embodiment to produce diphenylmethane, the alkyl halide is dichloromethane. In another preferred embodiment to produce diphenylmethane, the aromatic halide is benzyl chloride. A substituted benzene can be used in place of the benzene indicated above in other reactions. One benefit of the present invention is that it also provides a system and method which enables alkylation at high temperatures (greater than 100 degrees Celsius for this type of reaction), providing a commercially attractive period of time for completion of alklyation, while maintaining high selectivity for useful products such as diphenylmethane.

Useful organoaluminum catalysts can be selected from the group consisting of ethylaluminum dichloride (CAS registry 563-43-9) and methylaluminum dichloride (CAS registry 917-65-7). In one embodiment of the present invention, preparation of diphenylmethane (CAS registry 101-81-5) by reacting benzene (CAS registry 71-43-2) and dichloromethane (CAS registry 75-09-2) in the presence of either ethylaluminum dichloride or methylaluminum dichloride has provided a new and economically effective methodology for manufacture of diphenylmethane. The synthesis of diphenylmethane is the initial step in the series of chemical manufacturing steps used to manufacture fluorene (CAS registry 86-73-7) and fluorenyl derivatives such as 9,9-bis-(4-hydroxyphenyl)fluorene (BHPF) (CAS registry 3236-71-3). BHPF has further application in the manufacture of copolycarbonate resins. The CAS registry numbers are taken from the Chemical Abstracts Service (CAS) Registry, Chemical Abstracts Service, 2540 Olentangy River Road, Columbus, Ohio, and are provided to help simplify identification of certain key compounds respective to the present invention.

The reactions described above can occur at a temperature which is between a lower limit of about 25 degrees Celsius and an upper limit of about 230 degrees Celsius; in this regard, the preferred temperatures are between a lower limit of about 50 degrees Celsius and an upper limit of about 230 degrees Celsius, and the most preferred temperatures are between a lower limit of about 50 degrees Celsius and an upper limit of about 200 degrees Celsius. The pressure of the reactor is preferably between a lower limit of about 10 psig and an upper limit of about 1000 psig; more preferably, the pressure is between a lower limit of about 10 psig and an upper limit of about 600 psig. The reaction environment preferably will also be characterized by a pressure which is proximate to the vapor pressure of the reactants at the temperature of the reaction environment, such that the reactants are substantially maintained in the liquid state.

In one embodiment of the apparatus used for effecting the present invention, the reaction is carried out in a continuously stirred tank reactor. In another embodiment of the apparatus used for effecting the present invention, the reaction is carried out in a vented continuously stirred tank reactor. In another embodiment of the apparatus used for effecting the present invention, the reaction is carried out in a vented reactor having a vapor space volume and operating pressure sufficient to remove vapors of catalyst deactivating reaction by-products from the continuously stirred tank reactor such that the activity of the organoaluminum catalyst is substantially improved over the case where a sealed and non-vented reactor is used.

DETAILED DISCUSSION OF THE INVENTION

Use of alkylaluminum halides in diarylalkane (e.g. diphenylmethane) synthesis is distinct from and presents significant technical advantages over heterogeneous and homogeneous catalysts, the latter represented, for example, by homogeneous Friedel-Crafts catalysts based on aluminum chloride. One useful aspect of this invention is that it helps to enable the achievement of alkylation at higher temperatures (greater than 100 degrees Celsius for this type of reaction) than may have been traditionally used in diarylalkane synthesis while maintaining high selectivity respecting the desired products in the set of compounds created by the alkylation.

Figure 1:
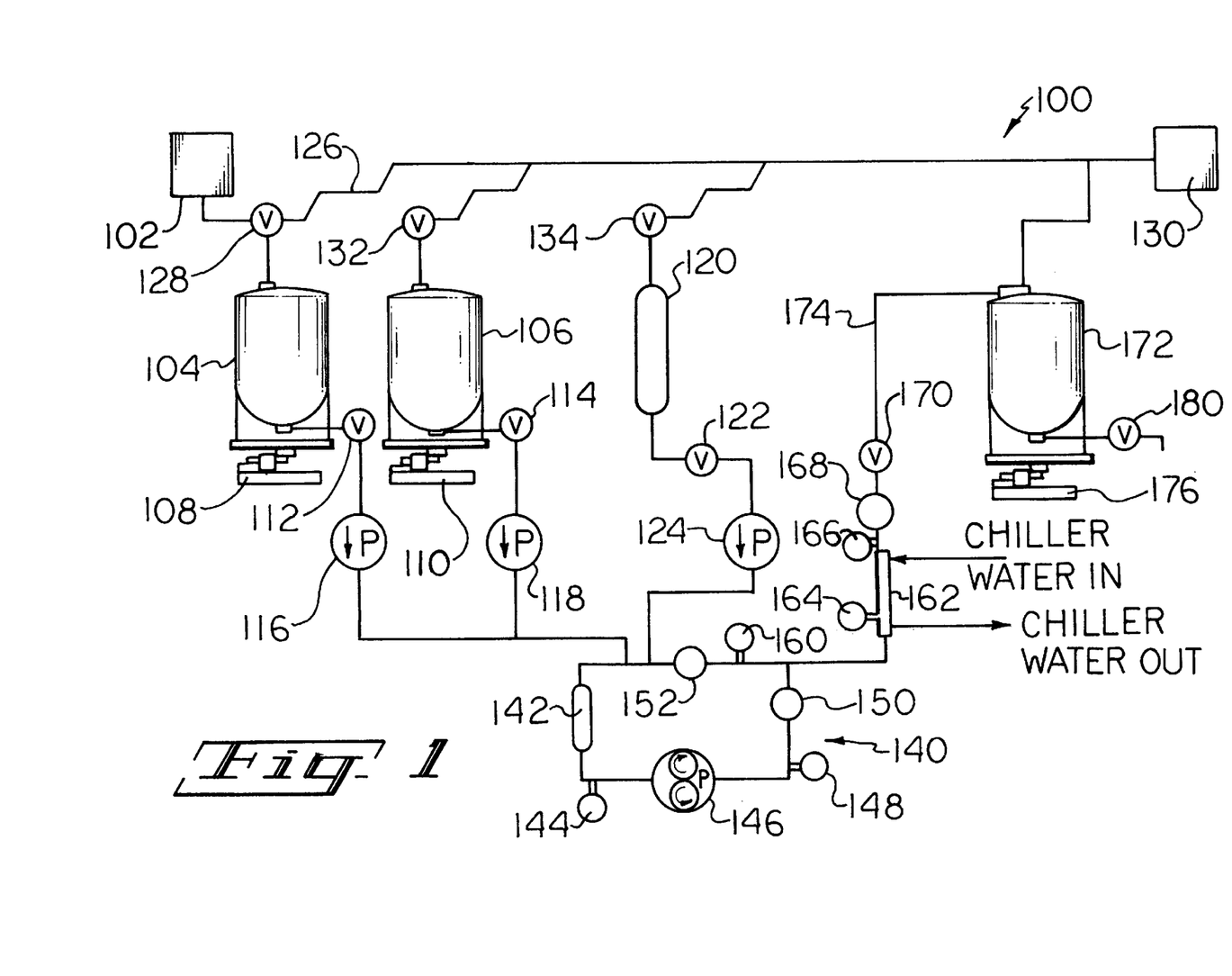
FIG. 1 presents an alkylation system for use in executing the present invention.

Turning now to an examination of FIG. 1, an alkylation system 100 is presented. Key components of the alkylation system are a benzene tank 104 for holding a charge of benzene (or substituted benzene), an alkylation agent tank 106 for holding either an alkyl or aromatic halide, a catalyst tank 120 for holding catalyst, a heated reactor loop 140, and a product neutralization vessel 172 for neutralizing byproduct hydrogen chloride in the product stream generated by the alkylation.

The benzene tank has a nitrogen block valve 128 for admitting nitrogen from nitrogen source 102 to purge oxygen from the benzene tank and/or pressurize the benzene tank. Benzene agent tank weighing system 108 measures the weight of the benzene tank, and benzene agent tank metering pump block valve 112 opens to feed benzene to benzene agent tank metering pump 116 which pumps the benzene to the heated reactor loop.

Similarly, the alkylation agent tank has a nitrogen block valve 132 for admitting nitrogen from the nitrogen source (via a line which is not shown but should be apparent) to purge and/or pressurize the alkylation agent tank. Alkylation agent tank weighing system 110 measures the weight of the alkylation agent tank, and alkylation agent tank metering pump block valve 114 opens to enable the alkyl halide or aromatic halide to feed alkylation agent tank metering pump 118 which pumps the alkylation agent to the heated reactor loop.

The catalyst tank has a nitrogen block valve 134 for admitting nitrogen from the nitrogen source (via a line which is not shown but should be apparent) to pressurize the catalyst in the catalyst tank. Catalyst tank metering pump block valve 122 opens to enable catalyst to move from the catalyst tank to catalyst tank metering pump 124 for feeding to the heated reactor loop.

(Note that block valves 134, 128, and 132 can be alternatively be turned to conduct nitrogen through the vent line to the flare 130.)

The heated reactor loop receives benzene or substituted benzene from benzene agent tank metering pump 116, alkyl halide or an aromatic halide from alkylation agent tank metering pump 118, and catalyst from catalyst tank metering pump 124 prior to heated reactor loop volumetric section 142 and passes these materials into heated reactor loop volumetric section 142. The temperature of the resultant alkylation mixture is monitored by temperature transmitter 144, and the alkylation mixture is circulated through the heated reactor loop by heated reactor loop circulation pump 146. The temperature of the alkylation mixture discharged from pump 146 is measured by a first temperature transmitter 148. After passing through pump 146, the pressure of the alkylation mixture is measured by pressure transmitter 150. The temperature of the alkylation mixture is further monitored between the pressure transmitter 150 and flow transmitter 152 by a second temperature transmitter 160 before the mixture flows through flow transmitter 152 as it returns to the inlet to the volumetric section 142.

The product stream is removed from the heated reactor loop into reactor product line 174 between pressure transmitter 150 and flow transmitter 152; the product stream passes from the heated reactor loop via product line 174 into the inlet to reactor product chiller 162. The chiller is cooled by chilled water and the temperature of the chiller 162 is monitored by a third temperature transmitter 164. The discharge temperature of the product stream is monitored by a fourth temperature transmitter 166 and pressure is monitored by pressure transmitter 168 prior to conveyance of the product stream through the product stream pressure control valve 170 which controls the back pressure on the heated reactor loop.

The product steam is neutralized by caustic soda in product neutralization vessel 172 to form neutralized product. The discharge end of product line 174 is immersed in a caustic soda (sodium hydroxide) solution resident within neutralization vessel 172. Neutralization vessel 172 is vented to the flare 130. The weight of neutralization vessel 172 is measured by weigh cell 176. The neutralized product is removed at discharge valve 180. Methods for further isolation of component compounds in the neutralized product should be apparent to those of skill.

The alkylation process according to the invention can be carried out in any batch-type or continuous alkylation reactor, such as for example a continuous stirred tank reactor, reactive distillation system, a turbulent flow alkylator reactor such as described in U.S. Pat. No. 5,227,556 to J. H. Benton, et al. entitled "Turbulent Flow Process, Monoalkyl Aromatic Production Process and Reactor for Such Process" (expressly incorporated herein by reference in describing one embodiment for implementing the present invention), and the like.

Preferably, the reactor is fit with a means for observing and controlling the temperature of the reaction, a means for observing and controlling the pressure of the reaction, and, optionally, a means for agitating the reactants. Benzene or substituted benzene may function as the solvent in the reaction while also having the purpose of being a reactant; alternatively, another chemical compound could function as the solvent in the reaction. The alkylating agent may be introduced in the liquid or gaseous state; and it may be added in entirety at the initiation of the reaction, or it may be fed in a (constant rate or variable rate) continuous manner into the reaction environment during the period of time between initiation and completion of a reaction operation.

It should also be noted that the catalyst could also be added in neat form or as a dilute solution in either benzene or other appropriate anhydrous solvent (i.e. hexane, isopentane, paraffin mixture, etc.). Use of a solvent is, for instance, often appropriate when ethylaluminum dichloride is the catalyst of choice, since concentrated ethylaluminum dichloride can be pyrophoric.

The contacting of the reactants in the presence of the catalyst may occur at any temperature or pressure which will produce the alkylated products of interest at high yield. The ratio of the benzene (or, in another embodiment, the substituted benzene) to the alkylating agent may vary depending on the identity of the alkylating agent and the nature of the environment in which the reaction occurs. In the alkylation of benzene with dichloromethane to produce diphenylmethane, it is preferable to use an excess of benzene in order to minimize the amount of by-products formed in the reaction. In the production of diphenylmethane, the molar ratio of benzene to dichloromethane is preferably between a lower limit of about 1 to and an upper limit of about 100, and, more preferably, between a lower limit of about 5 and an upper limit of about 25.

With respect to the environment in which the reaction operation occurs, the reaction may be effected in either a batch fashion, a plug-flow continuous fashion, or a backmix continuous fashion; the particular combination of reactants, catalyst(s), and chemical process arrangement (chemical engineering kinetic context "fashion" as noted above), and environmental conditions (such as temperature and pressure) are best established by generally apparent empirical methods. In the production of diphenylmethane, temperatures between a lower limit of about 25 and an upper limit of about 250 degrees Celsius, pressures between a lower limit of about 10 and an upper limit of about 1000 pounds per square inch, and catalyst concentrations from a lower limit of about 5 to an upper limit of about 5000 parts per million characterize the reaction environmnent attributes which should be considered in empirical investigation respecting the present invention. In the preferred embodiments, the use of an excess of benzene (or, in other embodiments, an excess of substituted benzene) is of benefit in minimizing by-products quantities formed from secondary reactions.

Preferred organoaluminum catalysts are ethylaluminum dichloride and methylaluninum dichloride.

In one embodiment of the present invention, a continuously stirred tank reactor is a useful vessel for containing the alkylation reaction. In another embodiment, an idealized optimal reactor enables removal of hydrogen chloride from the alkylation mixture to help control deactivation of the catalyst.

In a particular apparatus and process embodiment similar to that described with respect to FIG. 1, a series of alkylations of benzene with dichloromethane were conducted in a heated reactor loop (which was designed to have similar performance characteristics to a continuous stirred tank reactor). In these alkylations of benzene with dichloromethane, addition of reactants was controlled with a positive displacement metering pump. Benzene, dichloromethane, and catalyst were fed into the heated reactor loop where mixing, reaction, and recurrent circulation (recirculation) through the heated reactor loop were effected by pumping of the liquid reactants and catalyst with a seal-less gear pump. In each of the alkylation cases effected by use of that embodiment, careful measures were taken to confirm that moisture and air were essentially excluded to an acceptable minimum level of about 10 ppm $H_2O$ from the reactants, catalyst, and products during the course of the reaction operation so that the rate of reaction would not be suppressed by water or oxygen. The benzene and dichloromethane reactants were each passed through a molecular sieve bed to remove moisture (below the acceptable minimum level of about 10 ppm $H_2O$) before entry into the heated reactor loop. A typical reaction operation sequence was initiated with an initial loading and feeding with benzene and methylene chloride from separate storage vessels and separate metering pumps at the desired rates on a continuous basis until the heated reactor loop was liquid-full. The heated reactor loop was heated to the appropriate temperature having a value between a lower limit of 100 degrees Celsius and an upper limit of 151 degrees Celsius. Catalyst flow was initiated at the appropriate rate to achieve the desired concentration, which was verified by testing the effluent product stream from a discharge valve using an atomic absorption spectrophotometer. The particular embodiment was then operated continuously until approximately nine volumetric turnovers of the reactants, catalyst, and products had been achieved; the nine turnovers were used to reasonably assure that steady-state conditions had been achieved in the alkylation. Samplings of the reactants, catalyst, and product stream mixture were sequentially performed after each volumetric turnover during the duration of the reaction operation for each alkylation case. Hydrocarbon samples were immediately first hydrolyzed with water and then characterized by gas chromatography.

The following examples are given to illustrate the catalyst and the process of this invention and should not be construed as limiting its scope. All percentages are in mole percent unless otherwise indicated.

EXAMPLE 1

DIPHENYLMETHANE SYNTHESIS IN A RECIRCULATION REACTOR USING ETHYLALUMINUM DICHLORIDE AS CATALYST

In one alkylation case using the above-described method and the above described system, an alkylation of benzene with dichloromethane was performed at 151 degrees Celsius and 150 psig with a 25:1 benzene to dichloromethane molar ratio and a 10 minute residence time per turnover. Ethylaluminum dichloride was used as the organoaluminum catalyst at a concentration of 555 ppm. The ethylaluminum dichloride used in this example (and the remaining work related to the recirculation reactor) was a 25 wt/wt % solution of ethylaluminum dichloride in anhydrous benzene. Hence, in this example, a catalyst mixture of 25 weight % ethylaluminum dichloride in benzene was used at a ethylaluminum dichloride concentration of 555 ppm respective to the mixture of reactants, catalyst, and products. The dichloromethane conversion for this Example was determined to be 72.8 mole percent and the selectivity to diphenylmethane was determined to be 93.5 mole percent.

EXAMPLE 2

DIPHENYLMETHANE SYNTHESIS IN A LABORATORY GLASSWARE APPARATUS USING METHYLALUMINUM DICHLORIDE AS CATALYST

In another apparatus and process embodiment respective to the present invention, a series of alkylations of benzene with dichloromethane were conducted in laboratory glassware under an anhydrous nitrogen atmosphere in a batch kinetic context. In one of these alkylation cases, the alkylation of benzene with dichloromethane was performed at 50° C. at a 25:1 benzene to dichloromethane molar ratio by combining 500 milliliters benzene with 14 milliliters dichloromethane. A catalyst mixture of 2.2 milliliters of 1.0 M methylaluminum dichloride solution in hexane was used at a concentration of 555 ppm respective to the mixture of reactants, catalyst, and products. After a 60 minute reaction time, the dichloromethane conversion was 93.7 mole percent and the selectivity to diphenylmethane was 94.3 mole percent.

EXAMPLE 3

DIPHENYLMETHANE IN A LABORATORY GLASSWARE APPARATUS USING METHYLALUMINUM SESQUICHLORIDE AS CATALYST

In another example using the glassware of Example 2, the alkylation of benzene with dichloromethane was performed at 50° C. at a 25:1 benzene to dichloromethane molar ratio by combining 500 milliliters benzene with 14 milliliters dichloromethane. The catalyst was 2.2 milliliters of 1.0 M methylaluminum sesquichloride in toluene for a methyl aluminum sesquichloride concentration of 1008 ppm. After a 120 minute reaction time, the dichloromethane conversion was 97.8 percent and the selectivity to diphenylmethane was 94.2 percent.

Under similar reaction conditions, no reaction was observed with either dimethylaluminum chloride or trimethylaluminum. These results indicate that the reaction of benzene and dichloromethane is strongly influenced by the relative Lewis-acid strengths toward external base of the alkylaluminum chlorides, which increases in the order $R_3Al<R_2AlCl<R_3Al_2Cl_3<RAlCl_2$. In other words, ethylaluminum dichloride and methylaluminum dichloride performed more advantageously, respective to the purposes of the present invention, than the methylaluminum sesquichloride in the invention described in previously incorporated U.S. Pat. No. 3,787,512 to G. E. Nelson entitled "Preparation of Aromatic Hydrocarbons".

Present comparative process economics indicate that methylene chloride offers benefits over benzyl chloride and other potential feedstocks for manufacture of diphenylmethane. It should also be noted that, since alkylation catalysts which combine an aromatic reactant with an alkylating agent typically also will "transalkylate" said aromatic reactant with polyalkylated products, the present invention also has value in transalkylation of any polyalkylbenzene fraction from the effluent product stream generated by an alkylation operation.

Figure 2:
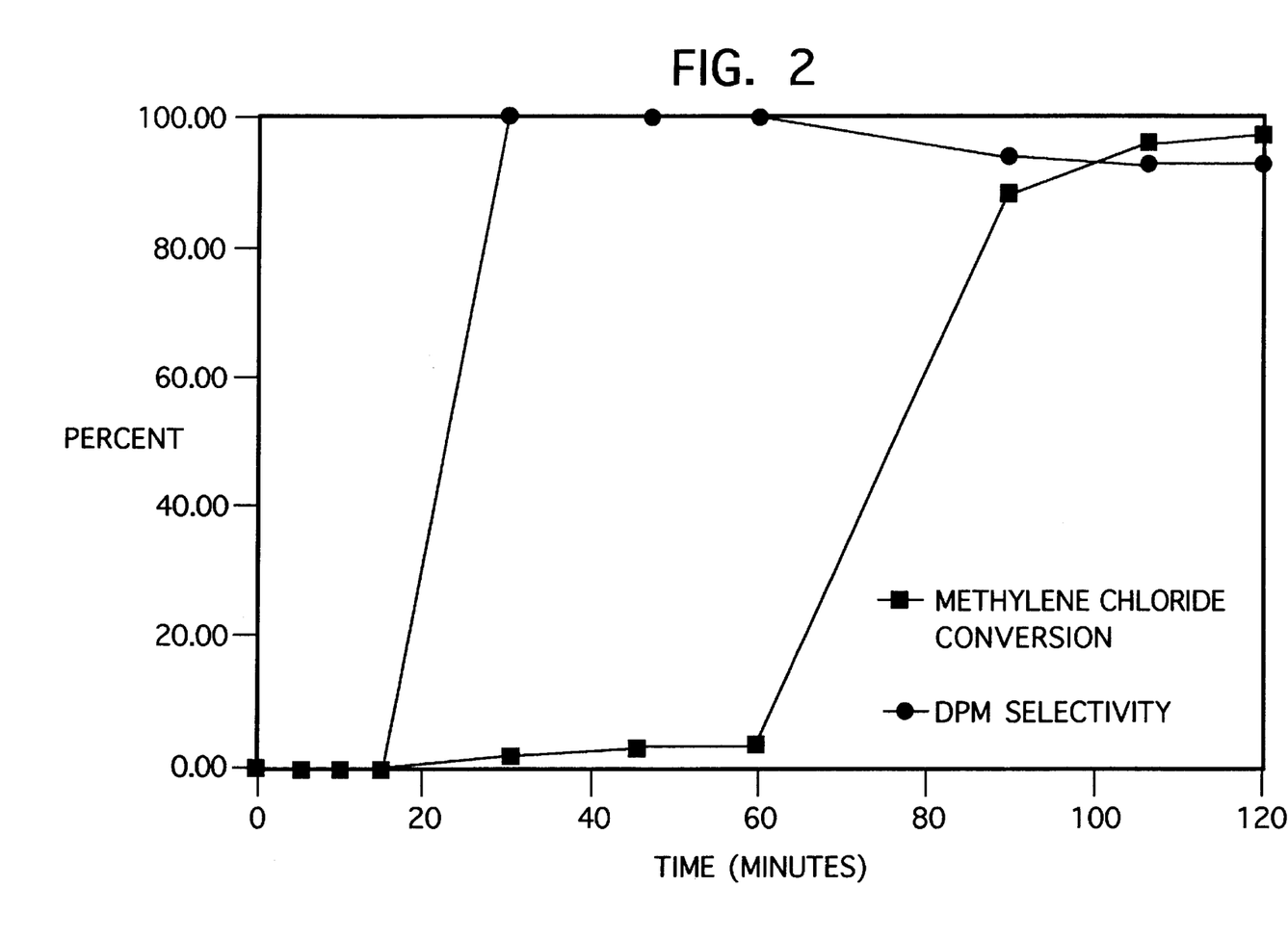
FIG. 2 presents rate of reaction results for the conversion of benzene and methylene chloride to diphenylmethane in the presence of methylaluminum sesquichloride.

FIG. 2 presents rate of reaction results for the conversion of benzene and methylene chloride to diphenylmethane in the presence of methylaluminum sesquichloride in glassware with a 25:1 benzene to methylene chloride feed ratio, a temperature of 50 degrees Celsius, and a methylaluminum sesquichloride concentration of 1008 parts per million. Five hundred milliliters of benzene were reacted with fourteen milliliters of methylene chloride. The methylaluminum sesquichloride was introduced as 2.24 milliliters of 1.0 molar methylaluminum sesquichloride in toluene.

Figure 3:
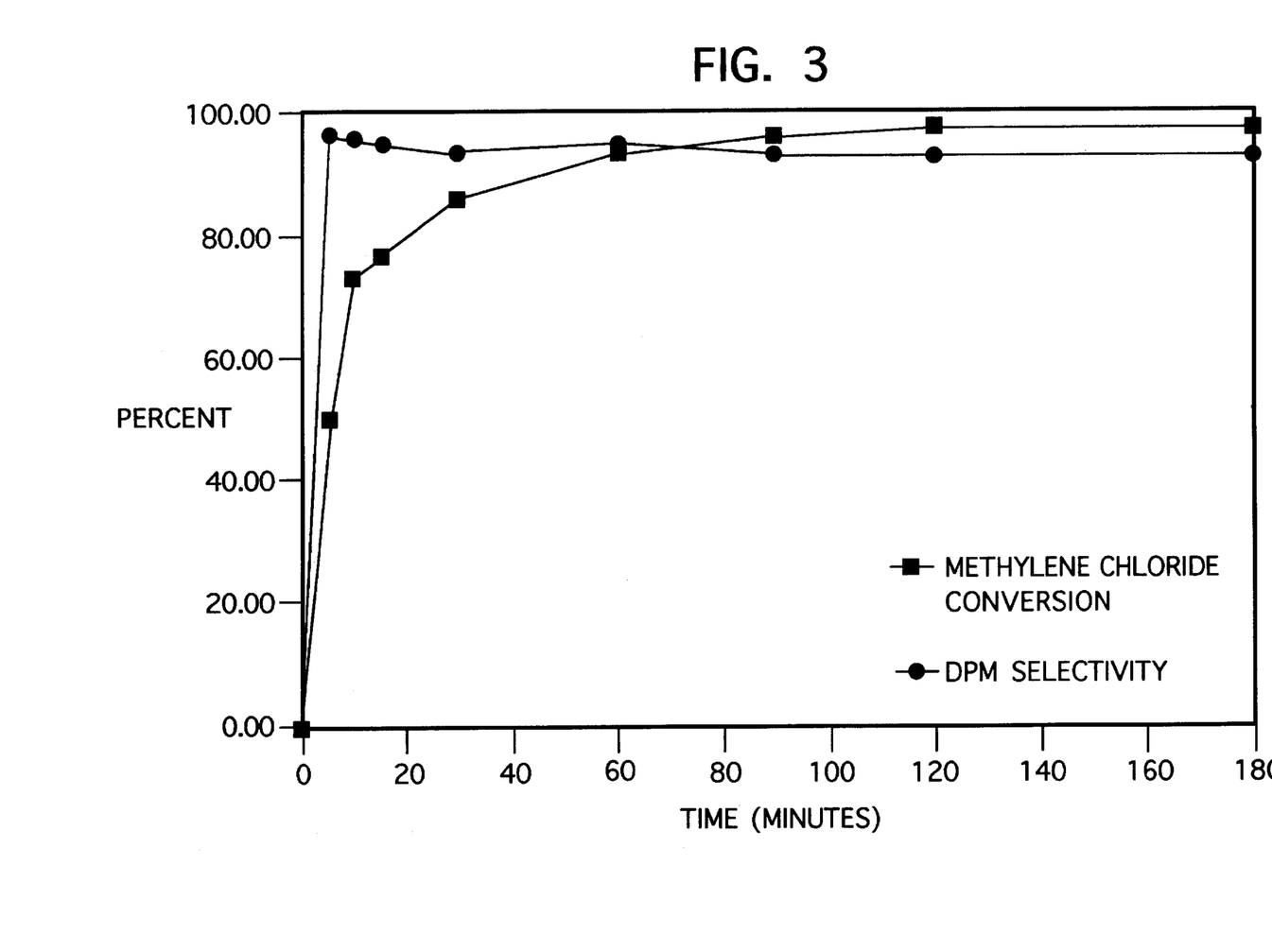
FIG. 3 presents rate of reaction results for the conversion of benzene and methylene chloride to diphenylmethane in the presence of methylaluminum dichloride.

FIG. 3 presents rate of reaction results for the conversion of benzene and methylene chloride to diphenylmethane in the presence of methylaluminum dichloride in glassware with a 25:1 benzene to methylene chloride feed ratio, a temperature of 50 degrees Celsius, and a methylaluminum dichloride concentration of 555 parts per million. Five hundred milliliters of benzene were reacted with fourteen milliliters of methylene chloride. The methylaluminum dichloride was introduced as 2.24 milliliters of 1.0 molar methylaluminum dichloride in hexane.

A comparison of FIGS. 2 and 3 clearly demonstrates the benefit of methylaluminum dichloride over methylaluminum sesquichloride as catalysts in the conversion of benzene and methylene chloride to diphenylmethane.

Figure 4:
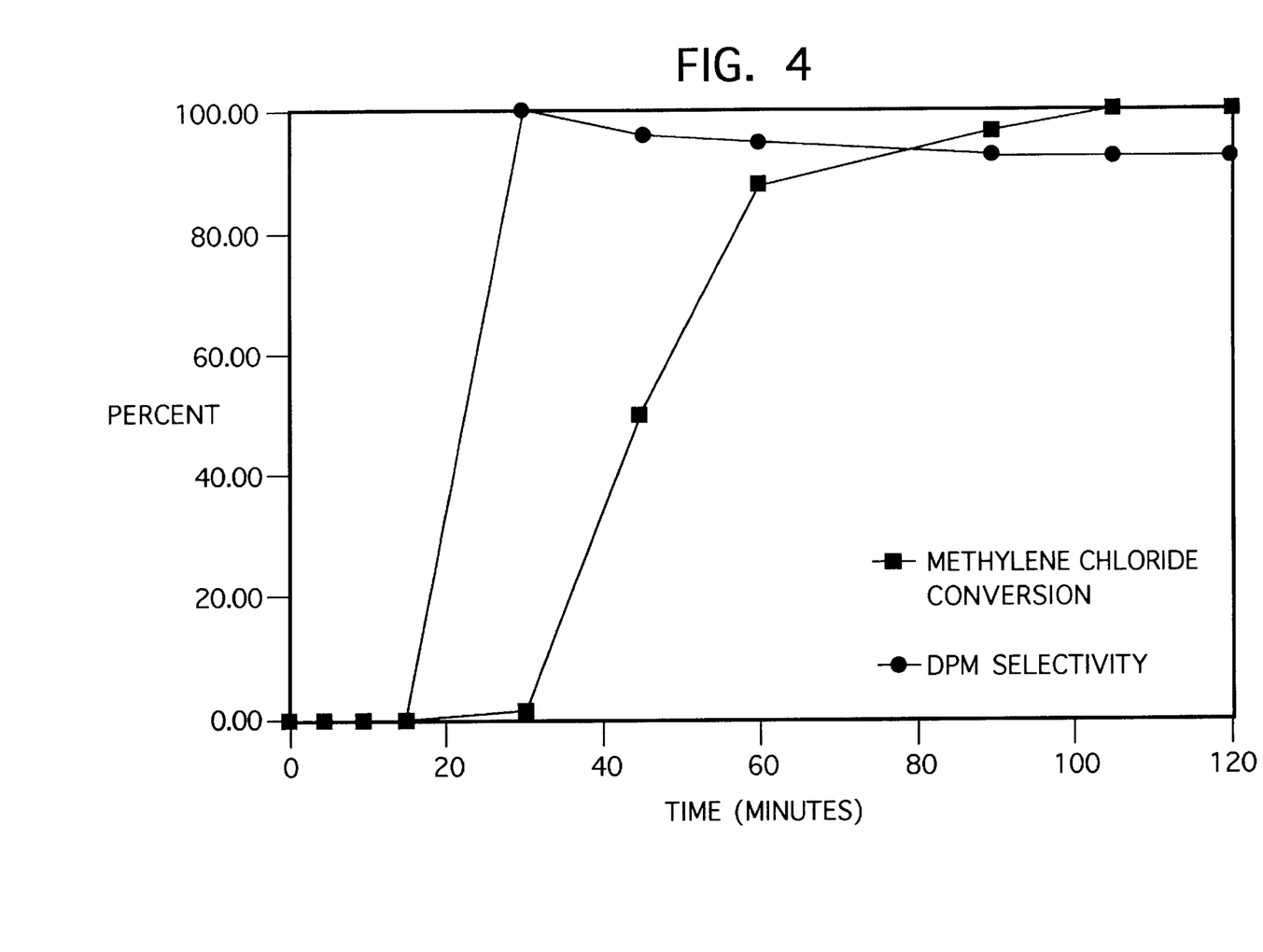
FIG. 4 presents rate of reaction results for the conversion of benzene and methylene chloride to diphenylmethane in the presence of ethylaluminum sesquichloride.

FIG. 4 presents rate of reaction results for the conversion of benzene and methylene chloride to diphenylmethane in the presence of ethylaluminum sesquichloride in glassware with a 25:1 benzene to methylene chloride feed ratio, a temperature of 50 degrees Celsius, and a ethylaluminum sesquichloride concentration of 1210 parts per million. Five hundred milliliters of benzene were reacted with fourteen milliliters of methylene chloride. The ethylaluminum sesquichloride was introduced as 2.45 milliliters of 25 weight percent of ethylaluminum sesquichloride in toluene.

Figure 5:
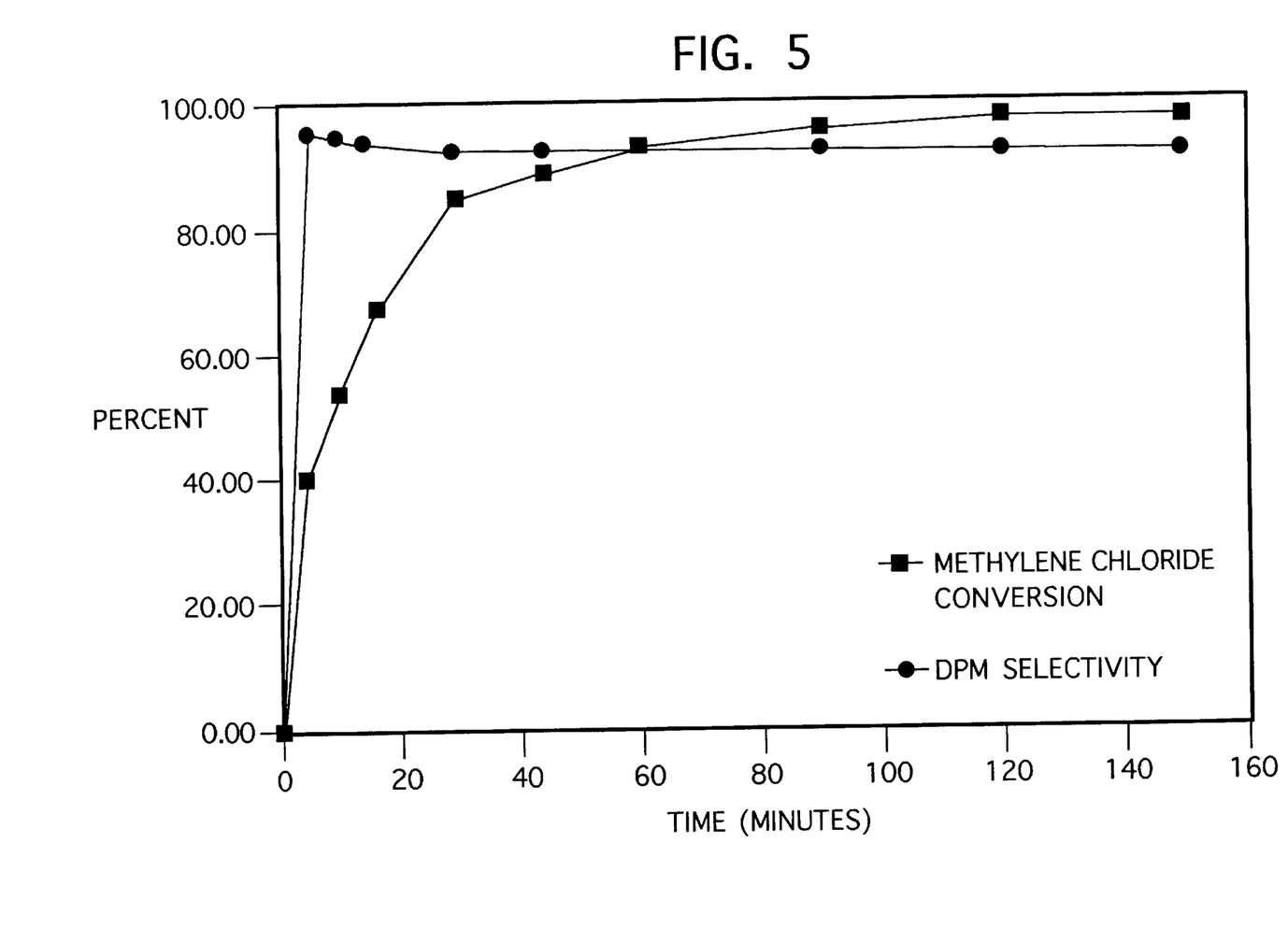
FIG. 5 presents rate of reaction results for the conversion of benzene and methylene chloride to diphenylmethane in the presence of ethylaluminum dichloride.

FIG. 5 presents rate of reaction results for the conversion of benzene and methylene chloride to diphenylmethane in the presence of ethylaluminum dichloride in glassware with a 25:1 benzene to methylene chloride feed ratio, a temperature of 50 degrees Celsius, and a ethylaluminum dichloride concentration of 623 parts per million. Five hundred milliliters of benzene were reacted with fourteen milliliters of methylene chloride. The ethylaluminum dichloride was introduced as 3.18 milliliters of 10 weight percent ethylaluminum dichloride in toluene.

A comparison of FIGS. 4 and 5 clearly demonstrates the benefit of ethylaluminum dichloride over ethylaluminum sesquichloride as catalysts in the conversion of benzene and methylene chloride to diphenylmethane.

The present invention has been described in an illustrative manner. In this regard, it is evident that those skilled in the art, once given the benefit of the foregoing disclosure, may now make modifications to the specific embodiments described herein without departing from the spirit of the present invention.

We claim:

1. A process for the preparation of a diarylalkane by reacting benzene and an alkyl halide in the presence ethylaluminum dichloride ormethylaluminumdichloride in a concentration from a lower limit of about 5 to an upper limit of about 5000 parts per million in a reactor system configured to provide a residence time of less than 15 minutes.

2. A process for the preparation of a diarylalkane by reacting benzene and an aromatic halide in the presence of ethylaluminum dichloride or methylaluminum dichloride in a concentration from a lower limit of about 5 to an upper limit of about 5000 parts per million in a reactor system configured to provide a residence time of less than 15 minutes.

3. A process for the preparation of a diarylakane by reacting substituted benzene and an alkyl halide in the presence of ethylaluminum dichloride or methylaluminum dichloride in a concentration from a lower limit of about 5 to an upper limit of about 5000 parts per million in a reactor system configured to provide a residence time of less than 15 minutes.

4. A process for the preparation of a diarylakane by reacting substituted benzene and an aromatic halide in the presence of ethylaluminum dichloride or methylaluminum dichloride in a concentration from a lower limit of about 5 to an upper limit of about 5000 parts per million in a reactor system configured to provide a residence time of less than 15 minutes.

5. The process as defined by claim 1 wherein said diarylalkane is diphenylmethane and said alkyl halide is methylene chloride.

6. The process as defined by claim 2 wherein said diarylalkane is diphenylmethane and said aromatic halide is benzyl chloride.

7. The process as defined by any of claims 1 to 6 wherein said preparation occurs at a temperature which is between a lower limit of about 25 degrees Celsius and an upper limit of about 230 degrees Celsius.

8. The process as defined by any of claims 1 to 6 further comprising:

receiving said benzene or substituted benzene, alkylhalide or an aromatic halide, and ethylaluminum dichloride or methylaluminum dichloride in a heated reactor loop in said reactor system;

passing said benzene or substituted benzene, alkylhalide or an aromatic halide, and ethylaluminum dichloride or methylaluminum dichloride into a heated reactor loop volumetric section in said heated reactor loop;

measuring the temperature of the output stream from said loop volumetric section with a first temperature transmitter;

circulating said volumetric section output stream through said heated reactor loop with a pump in said heated reactor loop;

measuring the temperature of the output stream from said pump with a second temperature transmitter;

measuring the pressure of said pump output stream;

further measuring the temperature of said pump output stream between said pressure transmitter and a How transmitter with a third temperature transmitter;

returning said pump output stream to said volumetric section; and removing a product stream from said heated reactor loop into a reactor product line connected to a reactor product chiller inlet.

* * * * *

UNITED STATES PATENT AND TRADEMARK OFFICE
CERTIFICATE OF CORRECTION

PATENT NO. : 5,977,422
DATED : November 2, 1999
INVENTOR(S) : Steven A. Costello et al.

Page 1 of 1

It is certified that error appears in the above-identified patent and that said Letters Patent is hereby corrected as shown below:

Column 9,
Line 10, after the "word" "dichloride" delete "ormethylaluminumdichloride" and insert therefore -- or methylaluminum dichloride --.

Signed and Sealed this

Twenty-fifth Day of December, 2001

Attest:

JAMES E. ROGAN
*Attesting Officer*  *Director of the United States Patent and Trademark Office*